United States Patent [19]

Schoolman

[11] 4,395,731

[45] Jul. 26, 1983

[54] TELEVISION MICROSCOPE SURGICAL METHOD AND APPARATUS THEREFOR

[76] Inventor: Arnold Schoolman, 8705 Catalina Dr., Prairie Village, Kans. 66207

[21] Appl. No.: 312,007

[22] Filed: Oct. 16, 1981

[51] Int. Cl.³ .............................................. H04N 9/54
[52] U.S. Cl. ...................................... 358/88; 358/93; 358/108; 350/518; 250/311; 128/4
[58] Field of Search ................... 358/93, 88, 107, 106, 358/108, 102, 91, 92; 128/4, 6; 280/311; 350/36, 37

[56] References Cited

U.S. PATENT DOCUMENTS

| | | |
|---|---|---|
| 2,955,156 | 10/1960 | Keilig . |
| 3,670,097 | 6/1972 | Janes . |
| 3,818,125 | 6/1974 | Butterfield ............................ 358/91 |
| 3,883,689 | 5/1975 | Mansour et al. . |
| 3,919,475 | 11/1975 | Dukick et al. . |
| 3,923,370 | 12/1975 | Mostrom . |
| 4,034,401 | 7/1977 | Mann . |
| 4,051,534 | 9/1977 | Dukich . |
| 4,115,802 | 9/1978 | Kramer et al. . |
| 4,153,913 | 5/1979 | Swift . |
| 4,160,263 | 7/1979 | Christy et al. . |
| 4,242,703 | 12/1980 | Lsuboshima et al. . |
| 4,246,607 | 1/1981 | V verberg . |

OTHER PUBLICATIONS

J. F. Butterfield "A Teaching Stereo-Video Microscope" SPIE vol. 66 (1975) Efficient Tran. of Patience Info.

Primary Examiner—Robert L. Griffin
Assistant Examiner—Edward L. Coles
Attorney, Agent, or Firm—Litman, Day & McMahon

[57] ABSTRACT

A method and apparatus therefor for providing an individual a magnified view of the manual manipulations of the individual, particularly those of a surgeon during surgery. Video cameras are provided for viewing the manual manipulations of the individual. Electric signals representing an image of the manual manipulations are transmitted to a video screen placed in optical alignment with eyes of the individual. The image viewed by the individual is selectively magnified and focused by the individual. An image other than that of manual manipulations of the individual can be transmitted to and projected on the video screen to provide the individual with additional visual information.

12 Claims, 10 Drawing Figures

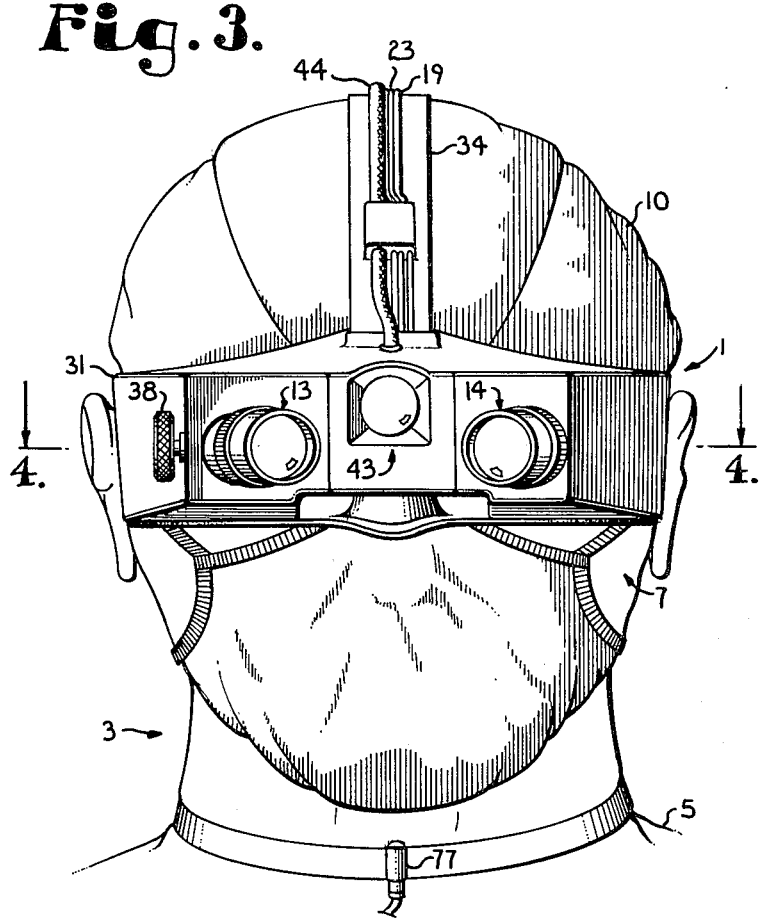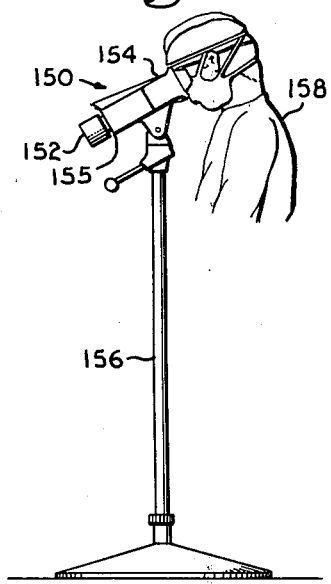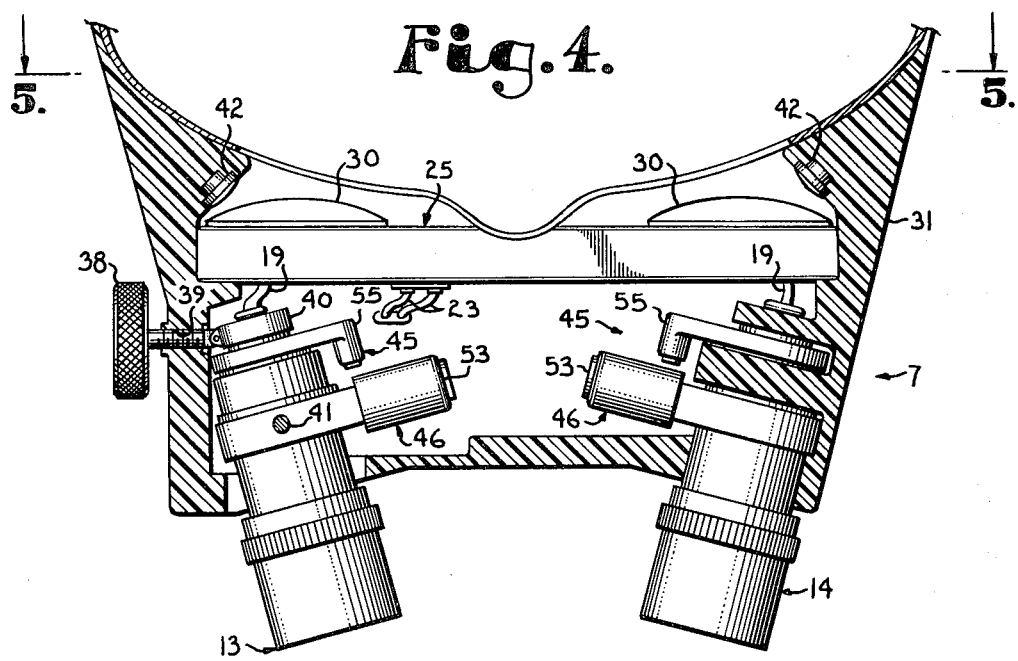

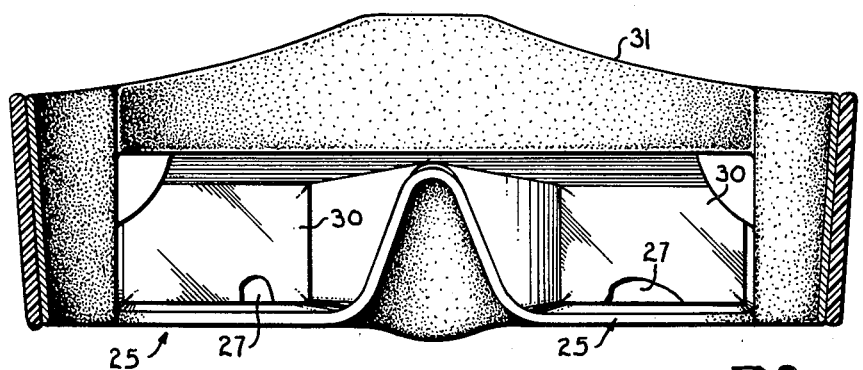
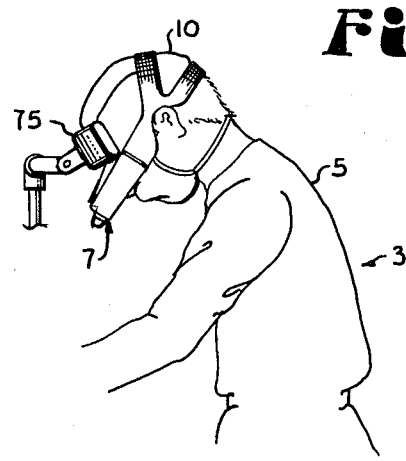
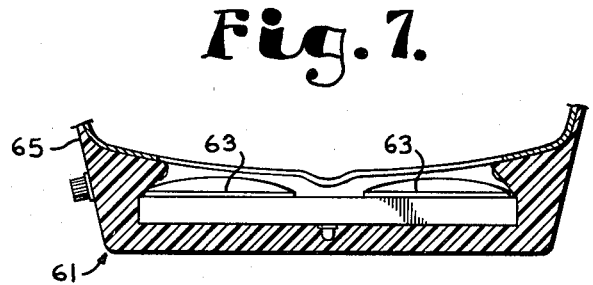
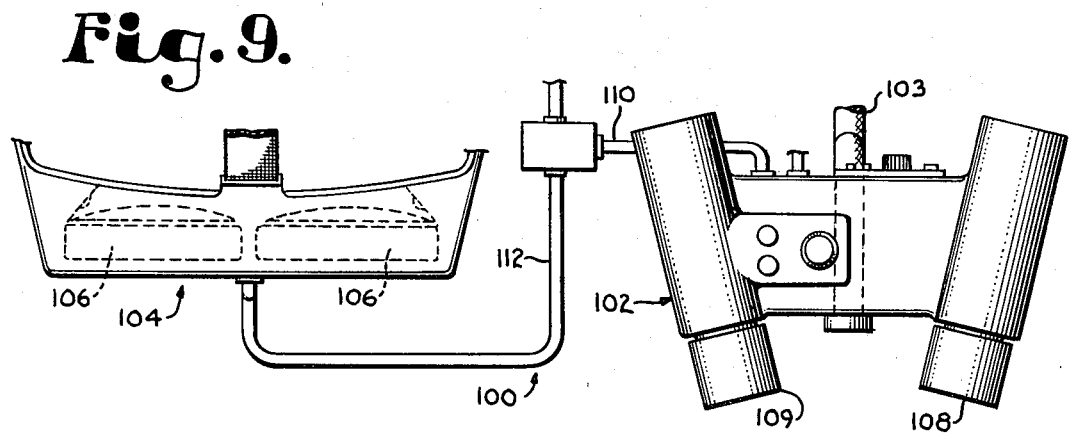

TELEVISION MICROSCOPE SURGICAL METHOD AND APPARATUS THEREFOR

BACKGROUND OF THE INVENTION

This invention relates to apparatus and methods for performing surgery and in particular to an apparatus and method for performing microscopic surgery.

In many types of surgery, such as neurosurgery, it is necessary for the surgeons to view the area upon which they are operating by means of a microscope. This is necessitated by the small size of the physiological elements upon which the doctors are performing surgery. In the past, such types of operations have been conducted with the aid of placing a microscope over the area upon which surgery is performed with the doctor viewing that area through the microscope. Such a method of performing surgery is quite cumbersome as the bulk and placement of the microscope does not allow free movement of the hands of the surgeons.

OBJECTS OF THE INVENTION

Therefore the objects of the present invention are: to provide an apparatus and method for performing microscopic surgery whereby the surgeon is allowed to have free movement of his hands; to provide such an apparatus which includes a pair of television cameras worn on the head of the surgeon and a pair of image projecting screens placed in optical alignment with eyes of the surgeon which project a magnified view of the image which is viewed by the television cameras; to provide a method of performing surgery which incorporates utilizing such cameras and viewing screens; to provide with such cameras and viewing screens focusing and zoom control means which are manipulable by a wearer of the cameras to provide the correct focus and magnification desired; to provide, associated with the viewing screen, means to project upon the screens an image other than that which is viewed by the viewing camera; to further provide with such an apparatus, a remote video camera which views an image displaced from the area of surgery such as an image in a pathology lab or an X-ray lab; to further provide such an apparatus which is easy to use, allows the surgeon free movement of his hands unfettered by apparatus protruding into the field of surgery, is durable in use and particularly well adapted for intended usage thereof.

Other objects and advantages of this invention will become apparent from the following description taken in connection with the accompanying drawings wherein are set forth, by way of illustration and example, certain embodiments of this invention.

SUMMARY OF THE INVENTION

A method and apparatus therefor is provided for performing microscopic surgery. The apparatus comprises a pair of video cameras which are retained on a head of a user thereof, generally a surgeon, by means of a headband or the like. The cameras are used to transmit electrical signals representing a stereoscopic view of manual manipulations of the user. The surgeon further retains on his head, in optical alignment with his eyes, a pair of viewing screens upon which are projected a selectively magnified view of that which is transmitted by the cameras. A suitable light means such as a fiber optic light source is further attached to the headband to adequately provide illumination on that area being viewed for the video transmission. The major electronics for the television camera and receiver units are housed in a console which is spaced apart from the surgeon. The surgeon can selectively vary the magnification of the image viewed on the screens and adjust the focus by means of foot pedals.

In using such an apparatus, the surgeon would have a much greater freedom of hand movement than with prior microscopic surgical apparatus and methods. As stated before in prior microscopic surgery, it was necessary for the surgeon to view the area of surgery by means of a microscope which was positioned close to and above the area of surgery so as to constantly obstruct the area of surgery. With the present apparatus, the surgeon will have much greater freedom of movement of his hands because the viewing screens and cameras are retained on a head of the surgeon in close proximity to his eyes and out of the way of his hands. Further, the image viewed by the surgeon can be selectively controlled to comprise not only a magnified view of the area of surgery, but also a view of other items such as pathology specimens or X-rays as they appear in the pathology lab or X-ray developing room. In doing so, the surgeon would not have to move from the patient, but could remain in close proximity to the patient and quickly receive other vital visual information relative to the patient.

An assistant of the surgeon can also be equipped with a suitable head gear which includes only the viewing screens placed in optical alignment with his eyes so that the assistant also views the same magnified image of the area of surgery as the surgeon views. A monitor can also be provided for other surgery team assistants, such as nurses, to enable them to more fully aid the surgeon in the operation.

The apparatus can further be used to aid other types of workers who must manually manipulate microscopic articles such as in constructing microelectronic devices.

The drawings constitute a part of this specification and include exemplary embodiments of the present invention and illustrate various objects and features thereof.

BRIEF DESCRIPTION OF THE DRAWINGS

FIG. 3 is a front elevational view of the apparatus and user.

FIG. 4 is an enlarged cross-sectional view of the apparatus taken generally along line 4—4 in FIG. 3.

FIG. 5 is an enlarged cross-sectional view of the apparatus showing viewing screens thereof taken generally along line 5—5 in FIG. 4.

FIG. 6 is a reduced side elevational view of a user having such an apparatus on his head showing a detente bar upon which the user can rest his head.

FIG. 7 is a generally cross-sectional view of a viewing screen adapted to be worn by an assistant to a wearer of a television microscope apparatus shown in FIGS. 1 through 6.

FIG. 9 is a generally top elevational, partially schematic diagram of a second embodiment of the present invention.

FIG. 10 is a side elevational view of a third embodiment of a television microscopic apparatus according to the present invention.

DETAILED DESCRIPTION OF THE PREFERRED EMBODIMENT

Figure 1:
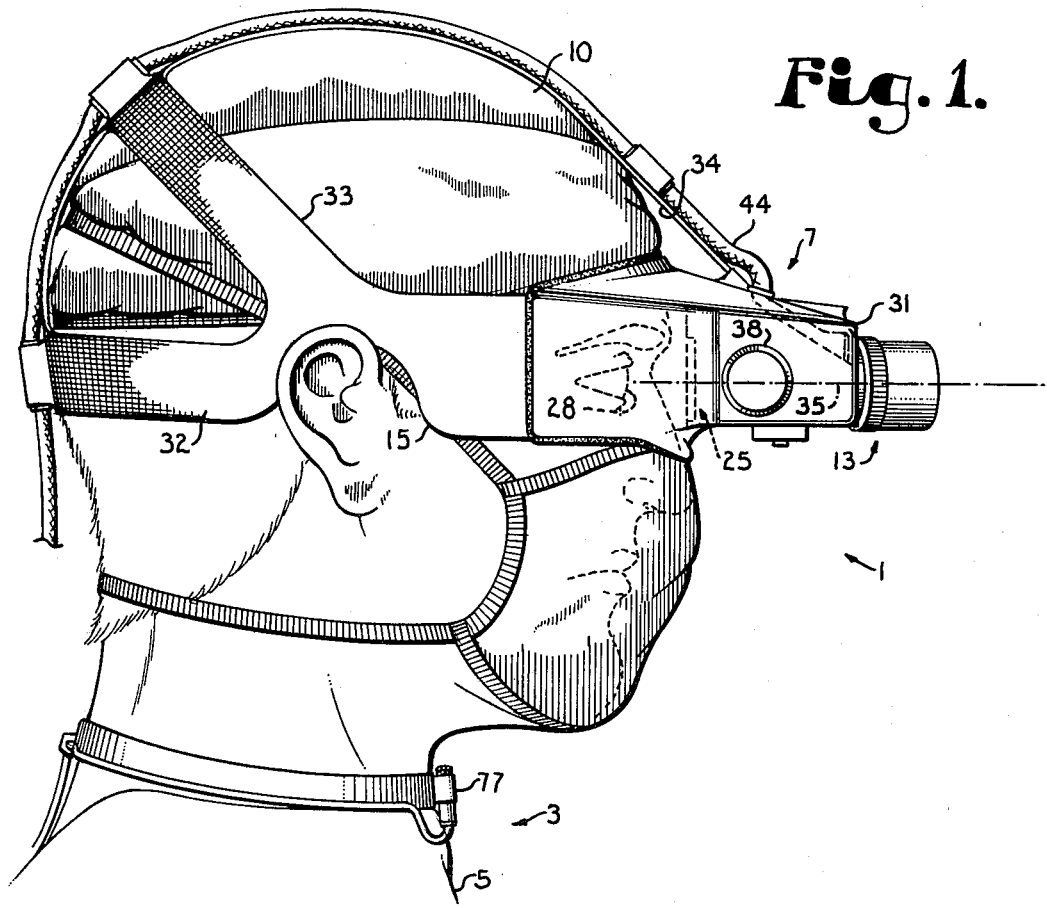
FIG. 1 is a side elevational view of a first embodiment of a television microscope apparatus for performing microscopic surgery according to the present invention shown being worn on a head of a user thereof.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a first embodiment of an apparatus for transmitting a magnified image of manual manipulations of a user 3 thereof. As shown herein, the user is a doctor 5 who is using such an apparatus 1 to aid himself in conducting microscopic surgery on a patient (not shown). It is understood that the user 3 could be any worker who requires a magnified view of that which he is working on, for example, as in microsurgery or as in fabricating microelectronic components and devices.

The apparatus 1 includes a television system 7 which is retained on a head 10 of a user 3 thereof. The television system 10 includes a pair of suitable image transmitting means such as vidicon cameras 13 and 14 which are attached to a headband 15 which rests on the head 10 of the user. The cameras 13 and 14 transmit electrical signals which represent an image of the area of surgery (not shown) which is that area wherein the doctor 5 is performing the manual manipulations. The cameras 13 and 14 have incorporated therewith suitable optical means to provide for a desired degree of magnification and focusing and are connected by suitable conduits 19 to a central console or video-audio distributor 21 in which is included the major electronic essentials of the television system 7.

In the distributor 21, the electronic signals representing the images that are viewed by the cameras 13 and 14, are generated and transmitted by suitable conduits 23 to a first image projection means 25 associated with the user 3. The image projection means 25 comprises two individual television screens 27 which are retained on the headband 15, and which are positioned each in optical alignment with an associated eye 28 of the user. A suitable lens 30 is positioned adjacent each television screen 27 to assure the doctor 5 can readily focus on the screens 27 without undue eye strain. As shown in FIGS. 1 through 5, the vidicon cameras, 13 and 14, and television screens 27 are both contained in a housing 31 which is attached to the headband 15.

The headband 15 as shown in FIG. 1 comprises bands 32, 33, and 34 which are fabricated of a resilient material and which fit snugly over head 10. Since the bands 32, 33 and 34 are resilient, the user 5 can selectively remove the video unit 31 from a position in optical alignment with his eyes 28 enabling the doctor to view the area of surgery (not shown) without the aid of the apparatus 1.

Figure 2:
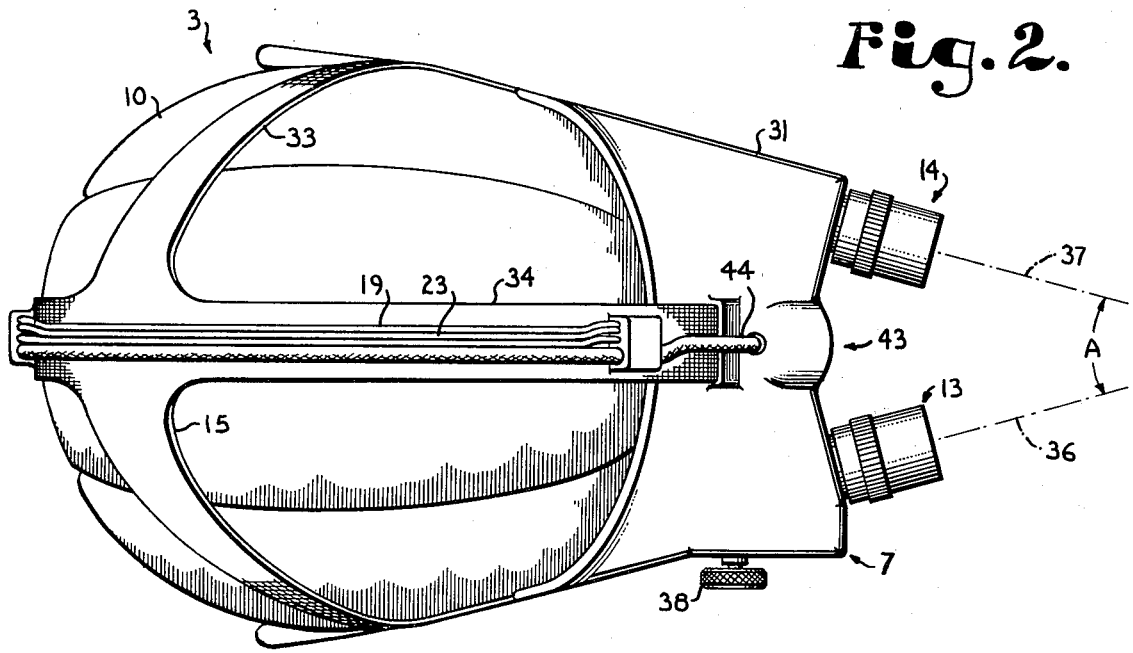
FIG. 2 is a top elevational view of the apparatus and user as shown in FIG. 1.
Figure 8:
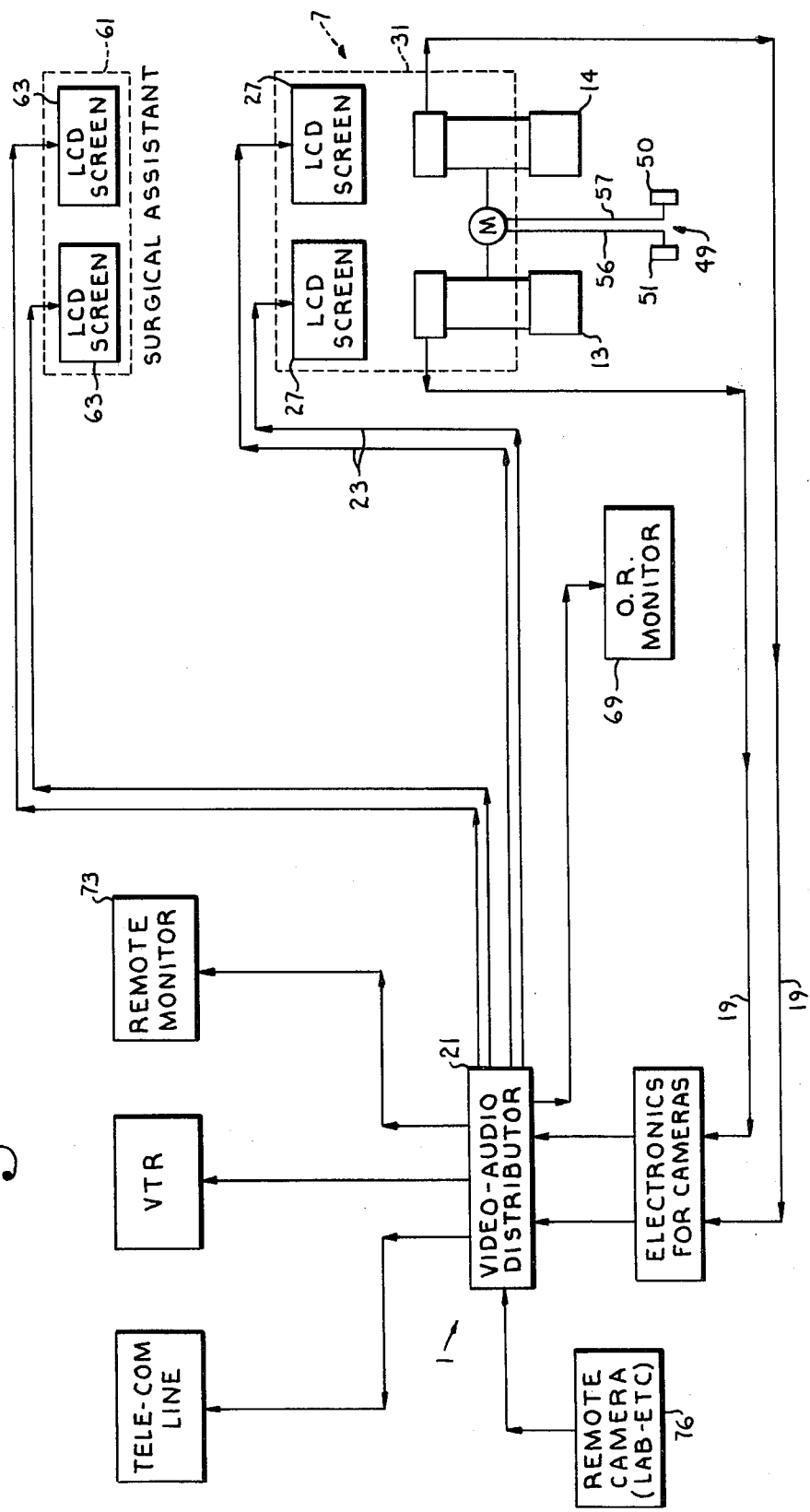
FIG. 8 is a block diagram showing schematically the electronic portion of the apparatus as set forth in FIGS. 1 through 7.

As shown in FIGS. 1 through 3, the television screens 27 are each placed directly in front of the eyes 28 of the user 3. Preferably, the images viewed by the user 3 on screens 27 will be stereoscopic. The cameras 13 and 14 are each placed in front of one of the television screens 27 and preferably, are directly in a normal line of sight 35 of the user 3 when the user 3 is working. This assures that the image viewed by the user 3 on screens 27 is seen from the same vantage point as if the user 3 were viewing his manual manipulations without the aid of an apparatus 1 as shown herein.

As shown in FIGS. 2, 3 and 4, one of the cameras, shown herein as the camera 13, rotates about an axis which is generally vertical and at right angles to the lines of sight 35 of the user. As such, an intersection angle A which is the angle of convergence between each line of view 36 and 37 of cameras 13 and 14 respectively, is adjustable allowing the user 3 to focus on items at varying distances from the cameras 13 and 14. An adjustment screw 38 received in a threaded bore 39 engages a rear portion 40 of the camera 13 to rotate the camera 13 about pins 41 which are received in associated bushings (not shown) in housing 31.

The television screens 27 are of high quality resolution and preferably capable of color reproduction. Likewise, the vidicon cameras 13 and 14 are preferably capable of transmitting electrical signals representing a color picture. A miniature television is currently being manufactured by Toshiba which has a liquid-crystal display screen measuring one and three-fifths of an inch by one and one-fifth of an inch. Such a television screen can be adapted to function as screens 27 herein. A suitable small light bulb 42 can be provided in a position to reflect light off each television screen 27 to form the images thereon.

An illumination means 43 is provided and retained on the headband 15 to provide illumination of the area of surgery. As shown herein, the illumination means 43 includes a variable intensity light source (not shown) positioned in the console 21 which is transmitted by means of fiber optic bundles 44 to the headband 15. The position of the illumination means 43 is best shown in FIG. 3 as being centrally located relative to the two cameras 13 and 14.

Image focusing adjustment means 45 and magnification adjustment means 46 are provided to selectively focus the image viewed on the television screens 27 and to provide a desired degree of magnification of the area of surgery. A foot control means 49 is provided and contains thereon two pedals 50 and 51 which are manipulable by a foot of a user 3 to control the focus and the degree of magnification of the image respectively. In this manner, the user 3 will be able to continually assure that the image he views through the television screen 27 is constantly in focus and of the desired degree of magnification.

As best shown in FIG. 4, the magnification adjustment means 46 includes a first servo motor 53 which selectively adjusts the magnification provided by the cameras 13 and 14. Likewise, the image focusing adjustment 45 includes a second set of servo-motors 55 which selectively adjust the focus of the image viewed on the screens 27. The magnification adjustment servo motor 53 is interconnected with foot pedal 51 by suitable electrical conduit 56. The focusing adjustment servomotors 55 are likewise interconnected with foot pedal 50 by suitable electrical conduit 57.

An assistant (not shown) can be provided with a viewer 61 shown in FIG. 7 which includes thereon two television screens 63 similar in design to television screens 27. The television screens 63 can be retained on a head of the assistant by means of a headband 65. The viewer 61 allows the assistant to view an image of the area of surgery which is identical to that viewed by the doctor 5. As such it is seen that it is not necessary for the assistant to have any camera incorporated into the viewer 61 which he is wearing.

A monitor 69 is provided in the operating room to allow other essential members of the surgery team, such as nurses (not shown), to view the area of surgery and the manipulations of the doctor 5 and assistant (not shown) to better prepare the nurses (not shown) to aid the doctor 5 and assistant (not shown). Other monitors 73 can be provided for viewing of the surgery by other personnel and students in a room remote from the operating room. It is noted that the image viewed on monitors 69 and 73 is the identical image that is viewed by the doctors since the same image is transmitted to the monitors 69 and 73 as is transmitted to television screens 27. As such, it is possible for the image of the area of surgery which is viewed by the television cameras 13 and 14 to be transmitted by suitable means such as microwave transmission or the like to a monitor (not shown) which is positioned at a great distance from the operating room. This allows the doctor 5 to consult with other doctors who are specialists in a certain field of surgery while the specialists are viewing the same view of the area of surgery which the doctor is.

In the use of that which is described in the first embodiment in FIGS. 1 through 8, the doctor 5 positions the apparatus 1 on his head in such a manner that the field of view of the cameras 13 and 14 is of the area of the surgery. After doing so, the doctor 5 is ready to conduct manual manipulations in the area of surgery. The foot control means 49 is positioned adjacent the operating table (not shown) such that while performing the operation, the doctor 5 can manipulate both pedals 50 and 51 with his feet. As such, the doctor 5 can selectively control the focus of the image received on the television screens 27 and the degree of magnification thereof. Since most operations are time consuming and since it is possible that the doctor 5 will grow tired of standing completely still in a certain position, a detente bar or stand can be provided stationarily affixed to a suitable object such as a floor of the operating room which detent stand 75 will enable the doctor to lean thereagainst, partially resting, but allowing the cameras 13 and 14 to continually be in proper viewing position of the area of surgery.

Since the television screens are mounted on a resilient headband 15, it is possible for the doctor to move the television screens 27 and cameras 13 and 14 out of his line of vision and allow the doctor to view an unobstructed and nonmagnified area of surgery.

At times, it is desirable that the image projected on the television screens 27 be different than the area of surgery. For instance, when a doctor 5 has removed a tissue specimen (not shown) which tissue specimen has been transported to a pathology lab for treatment, images of the treated specimen can be transmitted by means of an additional remote camera 76 to the television screens 27 to allow the doctor to receive visual information as to the condition of the pathology specimen. Further, images of developed X-ray samples can be transmitted to the television screens 27 to give the doctor 5 immediate results thereof. Suitable audio means such as microphone 77 can be provided to allow the doctor 5 to communicate with various other hospital personnel in the pathology lab and the X-ray lab to coordinate the switching of the image shown in the television screen 27. In order to accomplish this, an image switching means is contained in the console 21 or in another suitable place so that the doctor 5 or other suitable personnel can accomplish the desired switching at the desired time.

It is further seen that the apparatus 1 can be used to aid in teaching the students. For example, the students (not shown) and the doctor 5 equipped with similar apparatus 1 such as shown herein can be performing a similar operation with the student selectively viewing on a television screen 27 the image of the area of surgery (not shown) upon which the doctor-teacher is performing. Further, the doctor-teacher could selectively receive images of the surgery of each student. In doing so, the student can receive visual aids in performing the operation.

The reference numeral 100 generally represents a second embodiment of an apparatus shown in FIG. 9 according to the present invention and comprises an image transmitting unit 102 and an image projecting unit 104 which are not housed together. As disclosed in the second embodiment, the image transmitting unit 102 is positioned on a suitable stationary standard 103 and the image projecting unit 104 includes two television screens 106 and is retained on a head of a user (not shown) by a suitable headband (not shown) so as to retain each television screen 106 in optical alignment with an associated eye of the user. The image transmitting unit 102 includes two television cameras such as vidicon cameras 108 and 109 which transmit electrical signals representing the image viewed by them through appropriate conduits 110 to a central console (not shown), which houses the major electronics of the apparatus 100. The electrical signals are then transmitted from the central console through conduits 112 to the individual television screens 106 to project thereon an image viewed by the cameras 108 and 109. Suitable magnifying and focusing means (not shown) along with user activated controls (not shown) are provided as in the first embodiment of the present invention to allow the user of apparatus 100 to selectively magnify and focus the image transmitted to the television screens 106. Further, camera 109 is pivotally attached to the image viewing unit for varying the image viewing angle between the camera 108 and 109 to allow for proper focusing as in the first embodiment.

It is seen that the apparatus 100 as set forth herein allows the user thereof to hold on his head a much smaller and lightweight structure than before. This will aid the user in preventing fatigue. Further, since the cameras 108 and 109 are positioned on a stationary standard 103 the image viewed by the user on screens 106 is more stable. This further aids the user in performing the work.

FIG. 10 shows an apparatus 150 comprising a third embodiment of the present invention wherein both an image transmitting unit 152 and an image projecting unit 154 are contained in a unitary housing 155 which is positioned on a stationary standard 156 allowing a user 158 to freely move around without being constructed by the apparatus when he so desires. The housing 155 is substantially similar to housing 31 shown in FIGS. 1 through 6. As shown herein in FIG. 10, the standard 156 is positioned such that screens (not shown) comprising the image projecting unit 154 are viewable by the user 158 thereof. It is envisioned that the housing 155 could be stationarily supported by other means which allow total freedom of movement in front of the user 158, such as by being suspended from a ceiling by suitable support means.

It is to be understood that while certain forms of this invention have been illustrated and described, it is not to be limited to the specific form or arrangement of parts described and shown.

What is claimed and desired to secure by Letters Patent is:

1. A method of selectively providing an individual a magnified view of an image of manual manipulation of the individual and images of other than the manual manipulation of the individual, the method comprising:
   (a) viewing the manual manipulation by means of a video camera;
   (b) generating electrical signals by a first signal generating means representing a first image of said manual manipulation;
   (c) viewing a second image spaced from said manual manipulation by a second video camera;
   (d) generating electrical signals representing the second image by a second signal generating means;
   (e) positioning a viewing means in optical alignment with eyes of said individual;
   (f) signal transmittingly connected said viewing means with said first and second signal generating means; and
   (g) selectively regenerating by a signal selection means one of said first or second images on said viewing screen.

2. The method as set forth in claim 1 including the step of:
   (a) selectively magnifying said first image by image magnification adjustment means.

3. The method as set forth in claim 2 including the step of:
   (a) positioning said magnification adjustment means in close proximity to said individual so as to be manipulable by said individual.

4. A method of providing a magnified view of manual manipulation of an individual to that individual comprising the steps of:
   (a) viewing the manual manipulation by image transmitting means;
   (b) generating electrical signals representing an image of said manual manipulations;
   (c) positioning a first viewing means in optical alignment with said individual;
   (d) regenerating said image on said first viewing means;
   (e) selectively magnifying by magnification adjustment means the image regenerated on said first viewing means; and
   (f) placing said image transmitting means and said first viewing means in a unitary housing adapted to be worn on the head of the individual.

5. The method as set forth in claim 4 including the step of:
   (a) positioning said magnification adjustment means within close proximity to the individual enabling said individual to manipulate said magnification adjustment means.

6. The method as set forth in claim 4 including the step of:
   (a) placing said image transmitting means and said first viewing means in a line of sight of the individual.

7. The method as set forth in claim 4 wherein:
   (a) said image transmitting means comprises two vidicon cameras, and including the steps of:
   (b) positioning said cameras in said housing such that lines of view of each of the cameras converge defining an angle of convergence; and
   (c) rotating one of said cameras relative to the other to selectively vary said angle of convergence.

8. A television microscope apparatus comprising:
   (a) a television camera;
   (b) a television screen;
   (c) a video circuit interconnecting said camera and said screen, receiving a signal representative of an image sensed by said camera, and providing a signal representative of said image to said screen to reproduce said image thereon; and
   (d) head band means having said camera and said screen positioned thereon for sensing said image and reproducing said image substantially along the optical axis of one of the eyes of a wearer of said head band means.

9. An apparatus as set forth in claim 8 including:
   (a) a magnification control for adjusting the magnification of the image reproduced on said screen.

10. An apparatus as set forth in claim 8 including:
    (a) a stereoscopic pair of sets of said camera and said screen positioned on said head band means; and
    (b) a convergence control for adjusting the angle between the sets of said camera and screen to effect convergence of the axes of said sets at a selected distance in front of said cameras.

11. An apparatus as set forth in claim 8 including:
    (a) a remote television monitor connected to said video circuit and positioned remotely from said head band means.

12. An apparatus as set forth in claim 8 in combination with:
    (a) a head rest stand for engagement by the head of a wearer of said apparatus to facilitate steady viewing through said apparatus.

* * * * *